US010082475B2

(12) United States Patent
Hara et al.

(10) Patent No.: US 10,082,475 B2
(45) Date of Patent: Sep. 25, 2018

(54) X-RAY FLUORESCENCE SPECTROMETER

(71) Applicant: Rigaku Corporation, Tokyo (JP)

(72) Inventors: Shinya Hara, Takatsuki (JP); Takashi Matsuo, Takatsuki (JP); Yasujiro Yamada, Takatsuki (JP); Hisashi Honma, Takatsuki (JP); Yoshiyuki Kataoka, Takatsuki (JP)

(73) Assignee: Rigaku Corporation, Akishimi-shi, Tokyo (JP)

( * ) Notice: Subject to any disclaimer, the term of this patent is extended or adjusted under 35 U.S.C. 154(b) by 0 days.

(21) Appl. No.: 15/544,896

(22) PCT Filed: Aug. 26, 2016

(86) PCT No.: PCT/JP2016/075033
§ 371 (c)(1),
(2) Date: Jul. 20, 2017

(87) PCT Pub. No.: WO2017/038701
PCT Pub. Date: Mar. 9, 2017

(65) Prior Publication Data
US 2018/0106736 A1    Apr. 19, 2018

(30) Foreign Application Priority Data
Aug. 28, 2015   (JP) .................................. 2015-169543

(51) Int. Cl.
*G01N 23/223* (2006.01)
(52) U.S. Cl.
CPC ..... *G01N 23/223* (2013.01); *G01N 2223/076* (2013.01)

(58) Field of Classification Search
CPC .... G01N 23/00; G01N 23/22; G01N 23/2209; G01N 23/223; G01N 2223/00;
(Continued)

(56) References Cited

U.S. PATENT DOCUMENTS 5,062,127 A   10/1991   Sayama et al.
6,668,038 B2  12/2003   Kataoka et al.
(Continued)

FOREIGN PATENT DOCUMENTS

CN   1952652 A    4/2007
EP   0400396 A2  12/1990
(Continued)

OTHER PUBLICATIONS

Communication dated Sep. 12, 2017 from the Japanese Patent Office in counterpart Application No. 2017-537853.
(Continued)

*Primary Examiner* — Anastasia Midkiff
(74) *Attorney, Agent, or Firm* — Sughrue Mion, PLLC

(57) ABSTRACT

A scanning-type X-ray fluorescence spectrometer according to the present invention includes a quantitative analysis condition setting unit configured to determine whether or not to add, as an analytical element, a new detected element other than preset sample constituting elements, from an absorption-enhancement effect degree of fluorescent X-rays on an analytical value of an analytical element and an overlapping effect degree by an interfering line on an analytical line of the analytical element, on the basis of qualitative analysis results and semi-quantitative analysis results of standard samples.

4 Claims, 2 Drawing Sheets

(58) Field of Classification Search
CPC ......... G01N 2223/07; G01N 2223/076; G01N 2223/30; G01N 2223/303; G01N 2223/3037; G01T 1/368; G01T 7/00; G01T 7/005; G01J 3/00; G01J 3/02; G01J 3/0297; G01J 3/28; G01J 3/2803; G01J 3/44; G01J 3/4406; G01J 3/457; G01J 2003/283; G01J 2003/2833; G01J 2003/2843; G01J 2003/2866; G01J 2003/2873; G01J 2003/4424
See application file for complete search history.

(56) References Cited

U.S. PATENT DOCUMENTS

| | | |
|---|---|---|
| 6,845,147 B2 | 1/2005 | Elam et al. |
| 7,450,685 B2 | 11/2008 | Kataoka et al. |
| 2004/0066886 A1 | 4/2004 | Elam et al. |
| 2007/0086567 A1 | 4/2007 | Kataoka et al. |
| 2016/0258890 A1 | 9/2016 | Zarkadas et al. |

FOREIGN PATENT DOCUMENTS

| | | |
|---|---|---|
| JP | 2000-310602 A | 11/2000 |
| JP | 2002-340822 A | 11/2002 |
| JP | 2004-212406 A | 7/2004 |
| JP | 3567177 B2 | 9/2004 |
| JP | 2013-205080 A | 10/2013 |
| WO | 03/107037 A2 | 12/2003 |

OTHER PUBLICATIONS

Written Opinion of the International Searching Authority of PCT/JP2016/075033 dated Nov. 1, 2016.

International Search Report of PCT/JP2016/075033 dated Nov. 1, 2016.

Notification Concerning Documents Transmitted dated Sep. 5, 2017, issued by the International Bureau in International Application No. PCT/JP2016/075033.

Extended European Search Report dated Dec. 5, 2017, issued by the European Patent Office in counterpart European Application No. 16841733.5.

Communication dated Jan. 22, 2018, issued by the State Intellectual Property Office of the People's Republic of China in counterpart Chinese Application No. 201680006771.9.

International Search Report of PCT/JP2016/075034 dated Nov. 1, 2016.

X-RAY FLUORESCENCE SPECTROMETER

CROSS REFERENCE TO THE RELATED APPLICATION

This application is based on and claims Convention priority to Japanese patent application No. 2015-169543, filed Aug. 28, 2015, the entire disclosure of which is herein incorporated by reference as a part of this application.

BACKGROUND OF THE INVENTION

Field of the Invention

The present invention relates to a scanning-type X-ray fluorescence spectrometer which irradiates a sample with primary X-rays and measures intensities of generated secondary X-rays.

Description of Related Art

There has conventionally been a scanning-type X-ray fluorescence spectrometer that irradiates a sample with primary X-rays, measures intensities of secondary X-rays such as fluorescent X-rays generated from the sample, and performs a quantitative analysis of, e.g., contents of elements in the sample on the basis of the measured intensities. In such a spectrometer, standard samples corresponding to analytical samples are provided. Analytical elements of the analytical samples, and sample constituting elements and their contents (chemical analytical values) of each standard sample are preset as quantitative analysis conditions. Calibration curves are created by measuring the standard samples. And then the quantitative analyses of the analytical samples are performed.

Regarding setting of the quantitative analysis conditions, there has been an X-ray fluorescence spectrometer including a sample type storage unit, a semi-quantitative analysis unit, a type determining unit, and a quantitative analysis unit, wherein determination of a type of a sample based on a semi-quantitative analysis result and the quantitative analysis under analysis conditions appropriate for the determined type are automatically performed (see Patent Document 1). In addition, there has been an X-ray fluorescence spectrometer wherein, to calculate theoretical matrix correction factors for correcting a calibration curve, a correction model appropriate for a sample is set (see Patent Document 2). According to these spectrometers, the quantitative analysis conditions are automatically selected according to the type of the sample so that even an unskilled operator can accurately perform analysis.

RELATED DOCUMENT

[Patent Document]

[Patent Document 1] JP Laid-open Patent Publication No. 2002-340822

[Patent Document 2] JP Laid-open Patent Publication No. 2013-205080

However, in some cases, standard samples contain an element the content of which is unknown, and further, the contained element influences analysis of an analytical element, and thus causes an error. In this case, even with the above X-ray fluorescence spectrometers, the analytical element cannot be accurately analyzed because in presetting of the quantitative analysis conditions corresponding to the type of the sample, an element, the content of which is unknown, of the standard samples are not taken into consideration.

SUMMARY OF THE INVENTION

The present invention has been made in view of the above problems, and an object thereof is to provide a scanning-type X-ray fluorescence spectrometer that, even in a case where standard samples contain an element the content of which is unknown, can appropriately, automatically add the element to the analytical elements to quantitative analysis conditions so as to perform accurate analysis.

In order to achieve the aforementioned object, the present invention is a scanning-type X-ray fluorescence spectrometer which irradiates a sample with primary X-rays and measures intensities of generated secondary X-rays, and which includes a plurality of standard samples for creating calibration curves corresponding to analytical samples, and a quantitative analysis condition setting unit configured to preset, as quantitative analysis conditions, with analytical elements of the analytical samples, and sample constituting elements and their contents of each standard sample.

The quantitative analysis condition setting unit: performs a qualitative analysis and a semi-quantitative analysis, which is a quantitative analysis based on the qualitative analysis result, of each standard sample; detects, as a new detected element, an element other than the preset sample constituting elements, and calculates theoretical matrix correction factors, which are relevant to absorption-enhancement of the fluorescent X-rays, for the new detected element and the preset sample constituting elements by a fundamental parameter procedure (hereinafter, also referred to as "FP procedure"); calculates, as an absorption-enhancement effect degree, an effect degree of absorption-enhancement of the fluorescent X-rays by the new detected element on an analytical value of the analytical element, on the basis of the theoretical matrix correction factors, a semi-quantitative analytical value of the new detected element, and the preset contents of the sample constituting elements; and compares the absorption-enhancement effect degree with a corresponding predetermined reference value.

Further, the quantitative analysis condition setting unit: retrieves, from a prestored overlapping correction table, an overlapping correction factor for an interfering line of the new detected element with an analytical line of the analytical element; calculates, as an overlapping effect degree, an effect degree of overlapping by the interfering line of the new detected element on the analytical line of the analytical element, on the basis of the overlapping correction factor, the semi-quantitative analytical value of the new detected element, and the preset contents of the sample constituting elements; compares the overlapping effect degree with a corresponding predetermined reference value; and adds, when at least either the absorption-enhancement effect degree or the overlapping effect degree is greater than each corresponding predetermined reference value, the new detected element as an analytical element of the analytical samples to the quantitative analysis conditions.

According to the X-ray fluorescence spectrometer of the present invention, the spectrometer includes the quantitative analysis condition setting unit configured to determine whether or not to add, as the analytical element, the new detected element other than the preset sample constituting elements, from the absorption-enhancement effect degree of the fluorescent X-rays on the analytical value of the analytical element and the overlapping effect degree by the interfering line on the analytical line of the analytical element, on the basis of the qualitative analysis results and the semi-quantitative analysis results of standard samples. Accordingly, even when the standard samples include an element the content of which is unknown, the analytical element is appropriately, automatically added to the quantitative analysis conditions, so that accurate analysis can be performed.

In the X-ray fluorescence spectrometer of the present invention, it is preferable that, when the semi-quantitative analytical value of the new detected element is greater than a predetermined content, the quantitative analysis condition setting unit does not add the new detected element as the analytical element of the analytical samples to the quantitative analysis conditions, but sets the new detected element as a residue element in the quantitative analysis conditions. If the standard samples are steel, for example, iron as the main component should be set not as the analytical element but as the residue element. However, the iron may be detected as a new detected element. Thus, with this preferable configuration, such a new detected element is not added as the analytical element of the analytical samples but is set as the residue element on the basis of the semi-quantitative analytical value.

In the X-ray fluorescence spectrometer of the present invention, it is preferable that, for the new detected element to be added as the analytical element of the analytical samples, the quantitative analysis condition setting unit sets, in the quantitative analysis conditions, a quantitative calculation condition to be performed by the fundamental parameter procedure using a prestored apparatus sensitivity factor. As a quantitative calculation method for the new detected element to be added as the analytical element of the analytical samples, a calibration curve method may be used in which the semi-quantitative analytical value is set as the content of the added analytical element of the standard samples. However, the semi-quantitative analytical value, which is based on the X-ray intensity measured by scanning a goniometer, is not sufficiently accurate. According to this preferable configuration, the fundamental parameter procedure using the prestored apparatus sensitivity factors is applied, and the more accurate quantitative analytical value, which is based on the X-ray intensity measured with the goniometer being fixed, is used. Accordingly, analysis can be more accurately performed as a whole.

Any combination of at least two constructions, disclosed in the appended claims and/or the specification and/or the accompanying drawings should be construed as included within the scope of the present invention. In particular, any combination of two or more of the appended claims should be construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
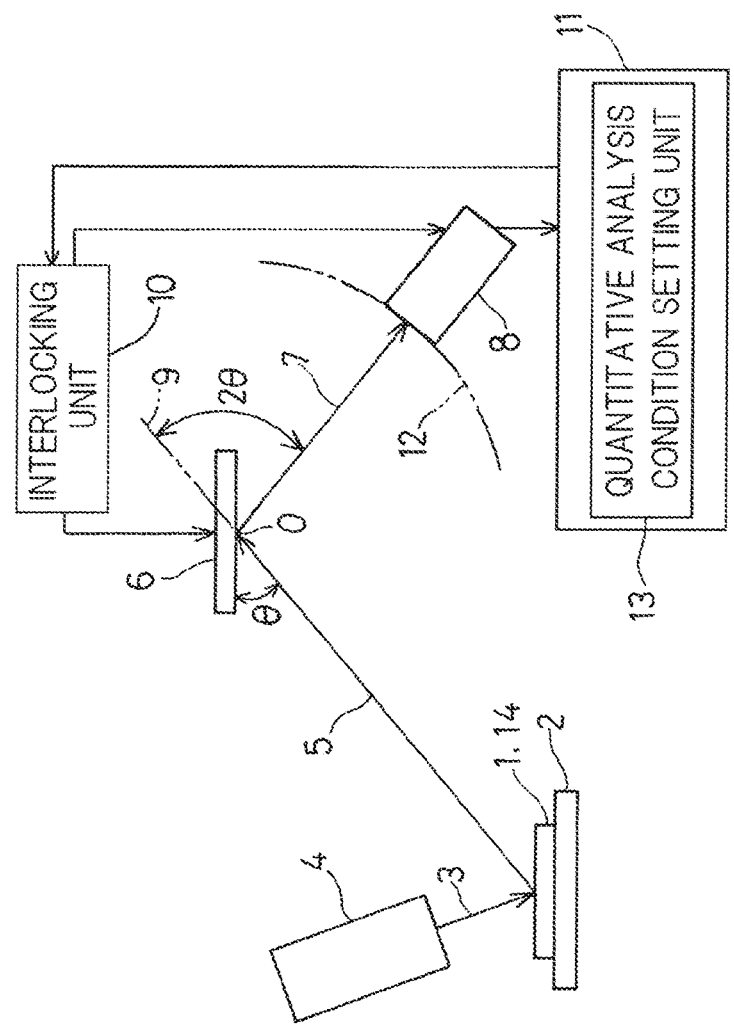
FIG. 1 is a schematic diagram illustrating an X-ray fluorescence spectrometer according to an embodiment of the present invention.

Hereinafter, a spectrometer according to an embodiment of the present invention is described with reference to the drawings. As illustrated in FIG. 1, the spectrometer is a scanning-type X-ray fluorescence spectrometer that irradiates sample 1, 14 with primary X-rays 3, and measures intensities of generated secondary X-rays 5. The spectrometer includes a sample stage 2 on which the sample 1, 14 is placed, an X-ray source 4 such as an X-ray tube configured to irradiate the sample 1, 14 with the primary X-rays 3, a spectroscopic device 6 which monochromates the secondary X-rays 5, fluorescent X-rays, generated from the sample 1, 14, and a detector 8 on which tertiary X-rays 7 monochromated by the spectroscopic device 6 are incident and which detects the intensity of the tertiary X-rays 7. An output from the detector 8 is inputted, through an amplifier, a pulse height analyzer, a counting unit, and to a control unit 11 configured to control the entire spectrometer.

The spectrometer is a wavelength dispersive and scanning type X-ray fluorescence spectrometer, and includes an interlocking unit 10, i.e., a so-called goniometer, configured to interlock the spectroscopic device 6 with the detector 8 so as to change a wavelength of the tertiary X-rays 7 incident on the detector 8. When the secondary X-rays 5 are incident on the spectroscopic device 6 at a certain incident angle $\theta$, an extended line 9 of the secondary X-rays 5 and the tertiary X-rays 7 monochromated by the spectroscopic device 6 form a spectroscopic angle $2\theta$, which is twice the incident angle $\theta$. To cause the tertiary X-rays 7, which are monochromated while the spectroscopic angle $2\theta$ is changed, to be incident on the detector 8 while changing the wavelength of the tertiary X-rays 7, the interlocking unit 10 rotates the spectroscopic device 6 around an axis O which passes a center of a surface of the spectroscopic device 6 and is perpendicular to the drawing sheet, and rotates the detector 8 around the axis O and along a circle 12 by an angle of twice the rotation angle of the spectroscopic device 6. The value of the spectroscopic angle $2\theta$ (angle $2\theta$) is inputted from the interlocking unit 10 to the control unit 11.

The spectrometer includes a plurality of standard samples 14 which are for creating calibration curves corresponding to analytical samples 1 and which have different compositions, and further includes, as a part of the control unit 11, a quantitative analysis condition setting unit 13 configured to be preset, as quantitative analysis conditions, with analytical elements of the analytical samples 1, sample constituting elements and their contents of each of the standard samples 14. The analytical sample 1 and the standard sample 14 are both referred to as the sample 1, 14.

The quantitative analysis condition setting unit 13 performs a qualitative analysis and a semi-quantitative analysis, which is a quantitative analysis based on the qualitative analysis result, of each of the standard samples 14, and detects, as a new detected element, an element other than the preset sample constituting elements. Here, the qualitative analysis refers to analysis in which a spectrum is obtained by measuring the intensities of the secondary X-rays 5 in a wide wavelength range under a predetermined standard analysis condition and peaks thereof are identified and analyzed. For example, spectrums of all the elements F to U are measured by scanning the goniometer 10, and the peaks detected from the measured spectrums are identified and analyzed. The semi-quantitative analysis refers to analysis in which the contents of the respective elements are determined on the basis of X-ray intensities measured by the qualitative analysis. The quantitative analysis refers to analysis in which, on the basis of X-ray intensities measured with the goniometer 10 being fixed respectively, the contents of respective elements are determined by using calibration curves corresponding to the analytical samples 1, or by a fundamental parameter procedure using prestored apparatus sensitivity factors.

Furthermore, the quantitative analysis condition setting unit 13 calculates, for the new detected element and the preset sample constituting elements, theoretical matrix correction factors, which are relevant to absorption-enhancement of the fluorescent X-rays, by a fundamental parameter procedure, and calculates, as an absorption-enhancement effect degree, an effect degree of absorption-enhancement of the fluorescent X-rays by the new detected element on an analytical value of the analytical element, on the basis of the theoretical matrix correction factors, the semi-quantitative analytical value of the new detected element, and the preset contents of the sample constituting elements, and compares the absorption-enhancement effect degree with a corresponding predetermined reference value.

Moreover, the quantitative analysis condition setting unit 13 retrieves, from a prestored overlapping correction table, an overlapping correction factor for an interfering line of the new detected element with an analytical line of the analytical element, and calculates, as an overlapping effect degree, an effect degree of overlapping by the interfering line of the new detected element on the analytical line of the analytical element, on the basis of the overlapping correction factor, the semi-quantitative analytical value of the new detected element, and the preset contents of the sample constituting elements, and compares the overlapping effect degree with a corresponding predetermined reference value.

When at least either the absorption-enhancement effect degree or the overlapping effect degree is greater than each corresponding predetermined reference value, the quantitative analysis condition setting unit 13 adds the new detected element as the analytical element of the analytical samples 1 to the quantitative analysis conditions.

In the X-ray fluorescence spectrometer according to the present embodiment, when the semi-quantitative analytical value of the new detected element is greater than a predetermined content, the quantitative analysis condition setting unit 13 does not add the new detected element as an analytical element of the analytical samples 1 to the quantitative analysis conditions, but sets the new detected element as a residue element in the quantitative analysis conditions.

In addition, in the X-ray fluorescence spectrometer according to the present embodiment, for the new detected element to be added as the analytical element of the analytical samples 1, the quantitative analysis condition setting unit 13 sets, in the quantitative analysis conditions, a quantitative calculation condition to be performed by the fundamental parameter procedure using a prestored apparatus sensitivity factor.

Figure 2:
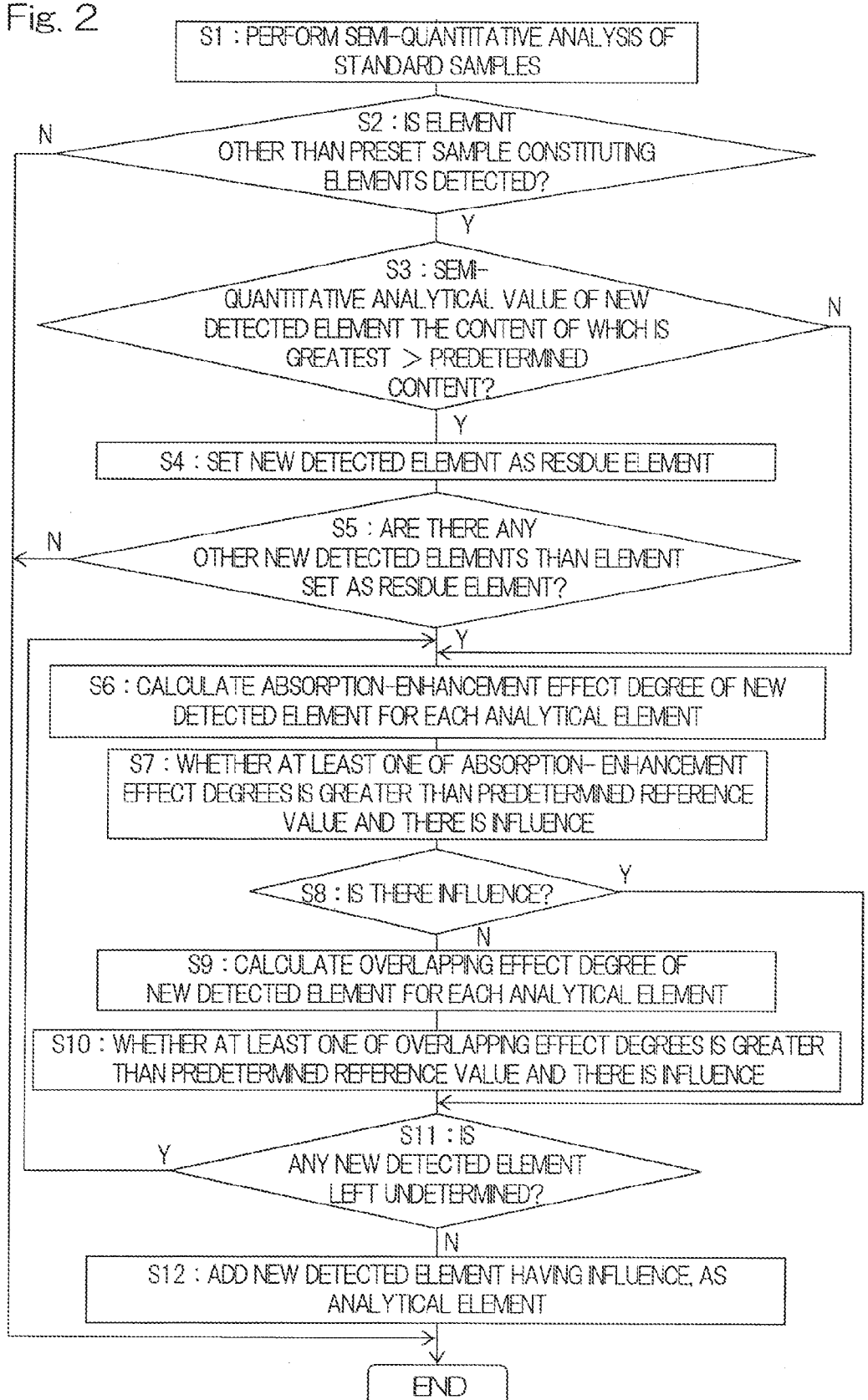
FIG. 2 is a flowchart showing operations of the X-ray fluorescence spectrometer.

The quantitative analysis condition setting unit 13 included in the X-ray fluorescence spectrometer according to the present embodiment specifically operates as shown in a flowchart in FIG. 2. In FIG. 2, YES and NO are abbreviated as "Y" and "N", respectively. As the quantitative analysis conditions, the analytical elements of the analytical samples 1, the sample constituting elements (which include the analytical elements of the analytical samples 1) and their contents of each of the standard samples 14, the overlapping correction table which is a table of the overlapping correction factors according to theoretical intensities determined for each possible combination of an analytical line and an interfering line, a sensitivity library which is a library of the apparatus sensitivity factors each determined from a ratio of a measured intensity obtained by measuring a pure substance, etc. and a theoretical intensity by an FP procedure for each representative element, and the like are preset in the quantitative analysis condition setting unit 13.

First, at step S1, the qualitative analysis and the semi-quantitative analysis, which is the quantitative analysis based on the qualitative analysis result, of each of the standard samples 14 are performed. Next, at step S2, when, as the semi-quantitative analysis results, any element other than the preset sample constituting elements is not detected, the operation is ended. When an element(s) other than the preset sample constituting elements is detected, the element(s) is regarded as a new detected element(s) and the flow proceeds to step S3.

Next, at step S3, whether the semi-quantitative analytical value of the new detected element, the content of which is the greatest, is greater than a predetermined content (for example, 50%) or not is determined. This is determination on whether the new detected element, the content of which is the greatest, is a main component or not. When the semi-quantitative analytical value for the greatest content is equal to or less than the predetermined content, the flow proceeds to step S6 (described later). When the semi-quantitative analytical value for the greatest content is greater than the predetermined content, the flow proceeds to step S4. Next, at step S4, the new detected element is not added as an analytical element of the analytical samples 1 to the quantitative analysis conditions, but is set as the residue element in the quantitative analysis conditions.

If the standard sample 14 is steel, for example, iron as the main component should be set not as the analytical element but as the residue element. However, the iron may be detected as a new detected element at step S2. Thus, steps S3 and S4 are performed so that such a new detected element is not added as the analytical element of the analytical samples 1 but is set as the residue element on the basis of the semi-quantitative analytical value.

Next, at step S5, whether or not there is any other new detected element than the new detected element set as the residue element at step S4 is checked. When there is no other new detected element, the operation is ended. When there is another new detected element, the flow proceeds to step S6. Next, at step S6, the theoretical matrix correction factors $\alpha_{ik}$, $\alpha_{ij}$, which are relevant to absorption-enhancement of the fluorescent X-rays, are calculated for the new detected element k and the preset sample constituting elements i, j, by the fundamental parameter procedure, and the effect degree of absorption-enhancement of the fluorescent X-rays by the new detected element k on the analytical value of the analytical element i is calculated as the absorption-enhancement effect degree $\Delta W_i/W_i$, through the following expression (1), on the basis of the theoretical matrix correction factors $\alpha_{ik}$, $\alpha_{ij}$, the semi-quantitative analytical value $W_k$ of the new detected element k, and preset contents $W_i$, $W_j$ of the sample constituting elements i, j.

$$\Delta W_i/W_i = \alpha_{ik} W_k/(1+\Sigma \alpha_{ij} W_j) \qquad (1)$$

In this calculation, all the new detected elements k are included in the sample constituting elements j, the average values of the respective contents and semi-quantitative analytical values of the plurality of standard samples 14 are basically used for the contents $W_i$, $W_j$ (including the semi-quantitative analytical values $W_k$ of the new detected elements k) of the sample constituting elements i, j. However, for the semi-quantitative analytical value $W_k$ of the new detected element k being determined in the absorption-enhancement effect degree $\Delta W_i/W_i$ of the expression (1), the maximum value among those of the plurality of standard samples 14 is used, and the contents $W_i$, $W_j$ (including the semi-quantitative analytical values $W_k$ of the new detected elements k being not determined) of the other sample constituting elements i, j are adjusted such that the total content of the contents $W_i$, $W_j$ and the semi-quantitative analytical value $W_k$ used as the maximum value becomes 100% (mass %, the same applies hereinafter).

Next, at step S7, when at least one of the absorption-enhancement effect degrees $\Delta W_i/W_i$ calculated for the respective analytical elements i is greater than the corresponding predetermined reference value, it is determined that the influence is significant, regarding the new detected element k being determined. Here, the corresponding predetermined reference value for the absorption-enhancement effect degree is, for example, 0.005 in the case where an average content of the analytical element i of the plurality of standard samples 14 is greater than 0.1%, and 0.02 in the case where the average content is equal to or less than 0.1%.

Next, at step S8, when it is determined at step S7 that the influence is significant, the flow proceeds to step S11 (described later). When it is determined at step S7 that there is no effect, the flow proceeds to step S9. Next, at step S9, the overlapping correction factor $^3\gamma_{ik}$ for an interfering line of the new detected element k with the analytical line of the analytical element i is retrieved from the prestored overlapping correction table, and the effect degree of overlapping by the interfering line of the new detected element k on the analytical line of the analytical element i is calculated as the overlapping effect degree $^3\gamma_{ik} {}^T I_k/{}^T I_i$ indicated by the following expression (2), on the basis of the overlapping correction factor $^3\gamma_{ik}$, a theoretical intensity $^T I_k$ of the interfering line of the new detected element k, and a theoretical intensity $^T I_i$ of the analytical line of the analytical element i.

$$^3\gamma_{ik} {}^T I_k/{}^T I_i \qquad (2)$$

Here, the theoretical intensity $^T I_i$ of the analytical line of the analytical element i and the theoretical intensity $^T I_k$ of the interfering line of the new detected element k are calculated, by the FP procedure, on the basis of the semi-quantitative analytical value $W_k$ of the new detected element k and the preset contents $W_i$, $W_j$ of the sample constituting elements i, j, as used at step S6.

Next, at step S10, when at least one of the overlapping effect degrees $^3\gamma_{ik} {}^T I_k/{}^T I_i$ calculated for the respective analytical elements i is greater than the corresponding predetermined reference value, it is determined that the influence is significant, regarding the new detected element k being determined. Here, the corresponding predetermined reference value for the overlapping effect degree is, for example, 0.005 in the case where the average content of the analytical element i of the plurality of standard samples 14 is greater than 0.1%, and 0.02 in the case where the average content is equal to or less than 0.1%, similarly to the corresponding predetermined reference values for the absorption-enhancement effect degrees $\Delta W_i/W_i$ at step S7.

Next, at step S11, whether or not any new detected element k is left undetermined is determined. When a new detected element k is left undetermined, the flow returns to step S6. When no new detected element k is left undetermined, the flow proceeds to step S12. Next, at step S12, the new detected elements k for each of which it is determined that the influence is significant are added as the analytical elements i of the analytical samples 1 to the quantitative analysis conditions, and the operation is ended.

For the new detected element k to be added as the analytical element i, any known content (chemical analytical value) is not set in the standard samples 14. Thus, as a quantitative calculation method for the analytical sample 1, a calibration curve method may be used in which, as the content of the added analytical element i of each standard sample 14, the semi-quantitative analytical value $W_k$ of this element (the new detected element k) obtained at step S1 is set. However, the semi-quantitative analytical value $W_k$, which is based on the X-ray intensity measured by scanning the by the goniometer 10, is not sufficiently accurate.

For this reason, in the X-ray fluorescence spectrometer according to the present embodiment, when the new detected element k for which it is determined that the influence is significant is added as the analytical element i of the analytical samples 1 at step S12, the quantitative analysis condition setting unit 13 sets, in the quantitative analysis conditions for the new analytical element i, the following quantitative calculation condition to be performed by the fundamental parameter procedure using the prestored apparatus sensitivity factor $k_i$. In this quantitative calculation, first, by the following expression (3), an X-ray intensity $I_{Mi}$ measured with the goniometer 10 being fixed is converted to a theoretical intensity scale by using the apparatus sensitivity factor $k_i$ read from a preset sensitivity library, to obtain a converted measurement intensity $^T I_{Mi}$.

$$^T I_{Mi} = k_i I_{Mi} \qquad (3)$$

Thereafter, repeated calculations (successive approximation calculations) through the following expressions (4) and (5) are performed under an appropriate convergence condition. Here, $^T I_{iP}$ represents a theoretical intensity when the analytical element i is contained as a pure substance at 100%, $W_i(0)$ represents the initial content, $W_i(n)$ represents the n-th content, $^T I_{in}$ represents a theoretical intensity for the analytical element i calculated from the composition obtained from the n-th contents of the respective elements, $W_i(n+1)$ represents the n+1-th content, that is, a quantitative analytical value.

$$W_i(0) = 100 \times {}^T I_{Mi}/{}^T I_{iP} \qquad (4)$$

$$W_i(n+1) = W_i(n) \times {}^T I_{Mi}/{}^T I_{in} \qquad (5)$$

Simultaneously with the repeated calculations through expressions (4) and (5), repeated calculations through the following expressions (6) and (7) using the calibration curve method are performed for the analytical elements i which are originally set as the quantitative analysis conditions. Here, A and B each represent a calibration curve constant, and $\alpha_j$ represents a theoretical matrix correction factor. In expressions (4) to (7), overlapping correction terms are omitted. In the repeated calculation through expression (5), as a part of the composition for calculating the theoretical intensity $^T I_{in}$, the n-th contents $W_i(n)$ obtained by expression (7) are used for the respective analytical elements i originally set as the quantitative analysis conditions. On the other hand, in the repeated calculation of expression (7), as the content $W_j(n)$ of a correction component, the n-th content $W_i(n)$ obtained by expression (5) is used for the new added analytical element i.

$$W_i(0) = A I_{Mi} + B \qquad (6)$$

$$W_i(n+1) = (A I_{Mi} + B)(1 + \Sigma \alpha_j W_j(n)) \qquad (7)$$

According to this configuration, the fundamental parameter procedure using the prestored analytical element $k_i$ is applied to the new added analytical element i, and the more accurate quantitative analytical value $W_i(n+1)$, which is based on the X-ray intensity $I_{Mi}$ measured with the goniometer 10 being fixed, is used. Therefore, analysis can be more accurately performed as a whole.

As described above, the X-ray fluorescence spectrometer according to the present embodiment includes the quantitative analysis condition setting unit 13 configured to determine whether or not to add, as the analytical element i, the new detected element k other than the preset sample constituting elements, from the absorption-enhancement effect degree $\Delta W_i/W_i$ of the fluorescent X-rays on the analytical value of the analytical element i and the overlapping effect degree $^3\gamma_{ik}{}^T I_k/{}^T I_i$ by the interfering line on the analytical line of the analytical element i, on the basis of the qualitative analysis result and the semi-quantitative analysis results of the standard samples 14. Accordingly, even when any of the standard samples 14 contains an element the content of which is unknown, the analytical element i is appropriately, automatically added to the quantitative analysis conditions, so that analysis can be accurately performed.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are to be construed as included therein.

REFERENCE NUMERALS

1 . . . analytical sample
3 . . . primary X-rays
5 . . . secondary X-rays
7 . . . tertiary X-rays
13 . . . quantitative analysis condition setting unit
14 . . . standard sample

What is claimed is:

1. A scanning-type X-ray fluorescence spectrometer which irradiates a sample with primary X-rays and measures intensities of generated secondary X-rays, the spectrometer comprising:
    a plurality of standard samples; and
    at least one hardware processor configured to implement:
        a quantitative analysis condition setting unit configured to be preset with quantitative analysis conditions, the quantitative analysis conditions comprising conditions of analytical elements of analytical samples, and the quantitative analysis conditions also comprising conditions of preset sample constituting elements, and their contents, of each of the standard samples, wherein
    the quantitative analysis condition setting unit is further configured to:
        perform a qualitative analysis and a semi-quantitative analysis, which is a quantitative analysis based on a qualitative analysis result, of each standard sample, and detect, as a new detected element, an element other than the preset sample constituting elements,
        calculate theoretical matrix correction factors, which are relevant to absorption-enhancement of fluorescent X-rays, for the new detected element and the preset sample constituting elements, by a fundamental parameter procedure, and calculate, as an absorption-enhancement effect degree, an effect degree of absorption-enhancement of the fluorescent X-rays by the new detected element on an analytical value of an analytical element, of the analytical elements, on a basis of the theoretical matrix correction factors, a semi-quantitative analytical value of the new detected element, and the contents of the preset sample constituting elements, and compare the absorption-enhancement effect degree with a corresponding predetermined reference value,
        retrieve, from a prestored overlapping correction table, an overlapping correction factor for an interfering line of the new detected element with an analytical line of the analytical element, and calculate, as an overlapping effect degree, an effect degree of overlapping by the interfering line of the new detected element on the analytical line of the analytical element, on a basis of the overlapping correction factor, the semi-quantitative analytical value of the new detected element, and the contents of the preset sample constituting elements, and compare the overlapping effect degree with a corresponding predetermined reference value, and
        add, when at least either the absorption-enhancement effect degree or the overlapping effect degree is greater than each corresponding predetermined reference value, the new detected element as an analytical element of the analytical samples to the quantitative analysis conditions.

2. The X-ray fluorescence spectrometer as claimed in claim 1, wherein
    when the semi-quantitative analytical value of the new detected element is greater than a predetermined content, the quantitative analysis condition setting unit does not add the new detected element as an analytical element of the analytical samples to the quantitative analysis conditions, but sets the new detected element as a residue element in the quantitative analysis conditions.

3. The X-ray fluorescence spectrometer as claimed in claim 1, wherein
    for the new detected element to be added as the analytical element of the analytical samples, the quantitative analysis condition setting unit sets, in the quantitative analysis conditions, a quantitative calculation condition to be performed by the fundamental parameter procedure using a prestored apparatus sensitivity factor.

4. The X-ray fluorescence spectrometer as claimed in claim 1, wherein the contents of the preset sample constituting elements comprise ones of percentages at which the contents are included in ones of the standard samples.

* * * * *